United States Patent [19]
Ducellier et al.

[11] Patent Number: 4,780,415
[45] Date of Patent: Oct. 25, 1988

[54] METHOD OF DEGRADING ORGANIC PRODUCTS, BY-PRODUCTS AND SCRAPS IN AN ANAEROBIC MEDIUM

[75] Inventors: Gilbert Ducellier, Colline de l'Estanove, Route de Laveurune Bat. D2, 34000 Montpellier; André Pavia, 408 rue Valéry Larbaud, 34100 Montpellier, France

[73] Assignees: Gilbert Ducellier; Andre Pavia; Union Industrielle et d'Entreprise; Valorga, all of France

[21] Appl. No.: 590,958

[22] Filed: Mar. 19, 1984

Related U.S. Application Data

[63] Continuation-in-part of Ser. No. 402,367, Jul. 27, 1982, abandoned.

[30] Foreign Application Priority Data

Jul. 29, 1981 [FR] France ................. 81 14740
Jul. 22, 1982 [FR] France ................. 82 12829
Sep. 1, 1983 [CA] Canada .................. 435894

[51] Int. Cl.⁴ .......................... C12P 5/00; C12M 1/02; C02F 3/30; C02F 3/08
[52] U.S. Cl. ..................................... 435/166; 435/267; 435/268; 435/316; 435/813; 210/218; 210/219; 210/603
[58] Field of Search ............... 435/166, 813, 316, 268, 435/267; 210/603, 218, 219

[56] References Cited

U.S. PATENT DOCUMENTS

| 3,630,848 | 12/1971 | Lefrancois | 435/316 |
| 4,001,090 | 1/1977 | Kalina | 435/316 |
| 4,057,401 | 11/1977 | Boblitz | 435/166 |
| 4,082,672 | 4/1978 | Petroski | 210/205 |
| 4,111,808 | 9/1978 | Fair | 210/197 |
| 4,334,998 | 6/1982 | Rios et al. | 210/617 |
| 4,482,458 | 11/1984 | Rovel et al. | 210/603 |
| 4,514,297 | 4/1985 | Enqvist | 210/194 |
| 4,579,654 | 4/1986 | Bremmer | 210/180 |

FOREIGN PATENT DOCUMENTS 7509057 3/1976 France .

Primary Examiner—Elizabeth Weimar
Attorney, Agent, or Firm—Steinberg & Raskin

[57] ABSTRACT

A method and apparatus for carrying out a degradation in an anaerobic medium, such as a methanogenesis, of organic products, by-products or waste from human, animal and/or plant origin, involving feeding said products to be degraded into a closed fermentation vessel, forcing said products to flow in a direction of circulation within said vessel and recovering the gas produced called biogas evolved above said body of degraded products, with the feeding and/or discharge of the products performed pneumatically, preferably through pneumatic thrust and, according to a preferred embodiment, by injection of gas, preferably biogas. A further improvement comprises using the biogas produced for homogenizing said body of products contained within said vessel, the pressure of injection being in relation to the actual density of the products, in the injection related section.

20 Claims, 6 Drawing Sheets

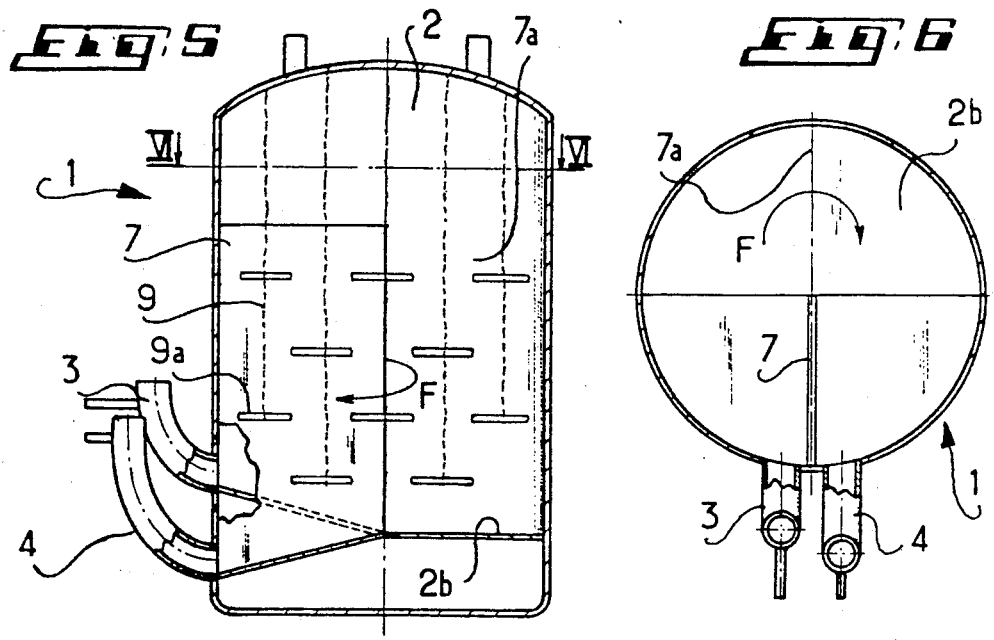
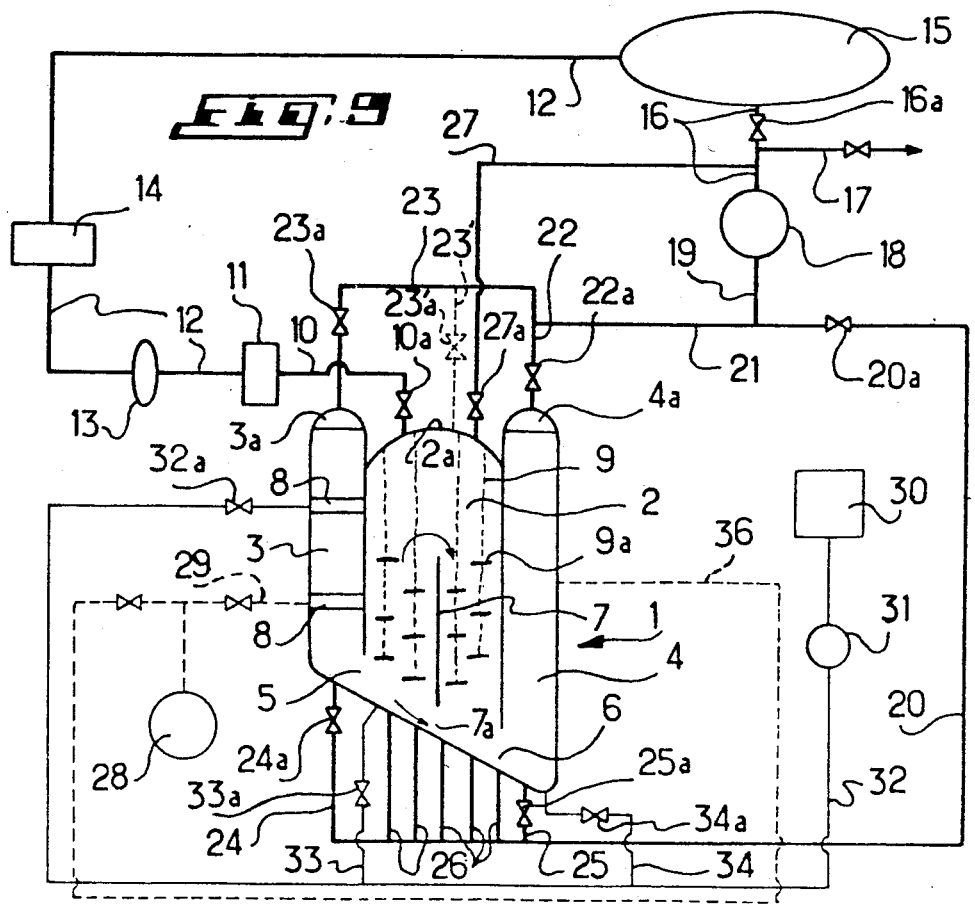

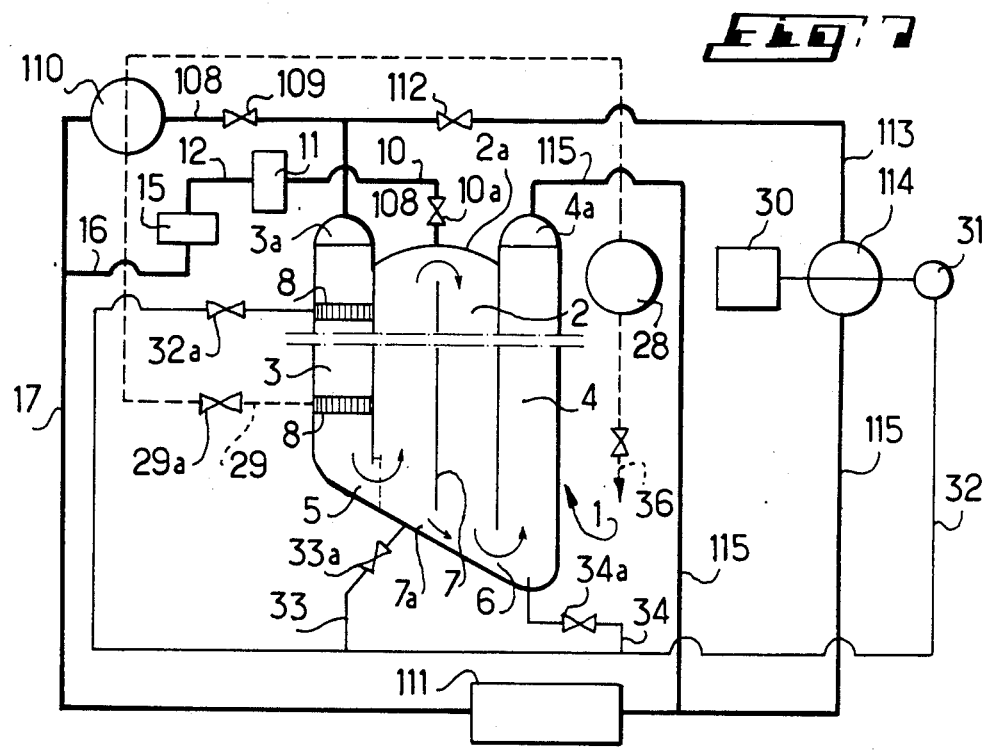
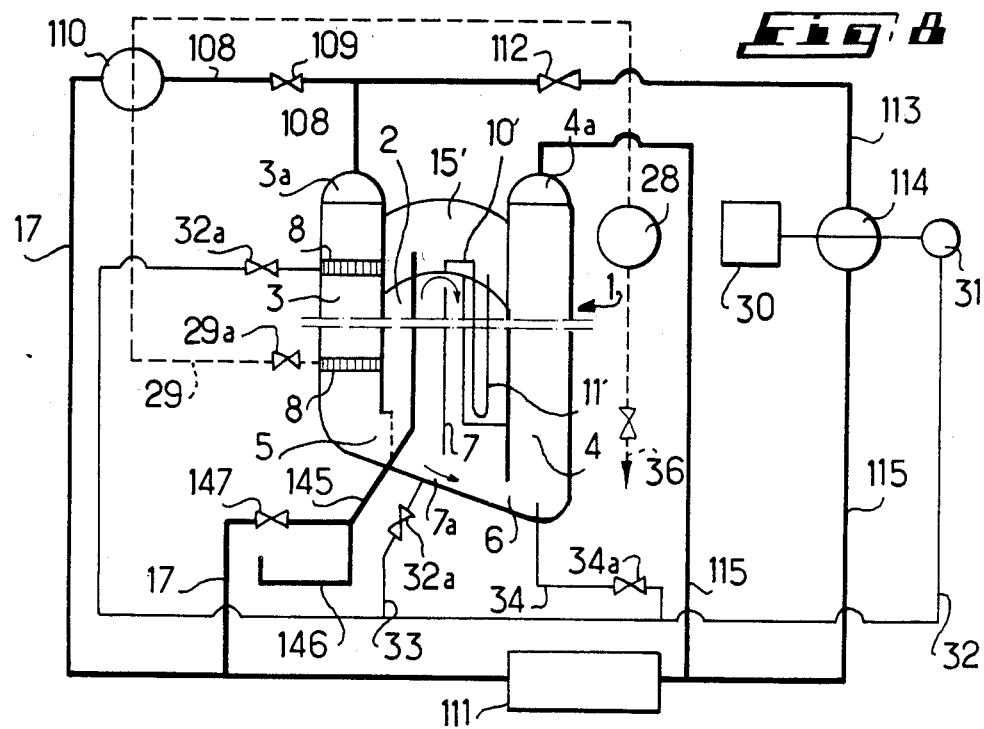

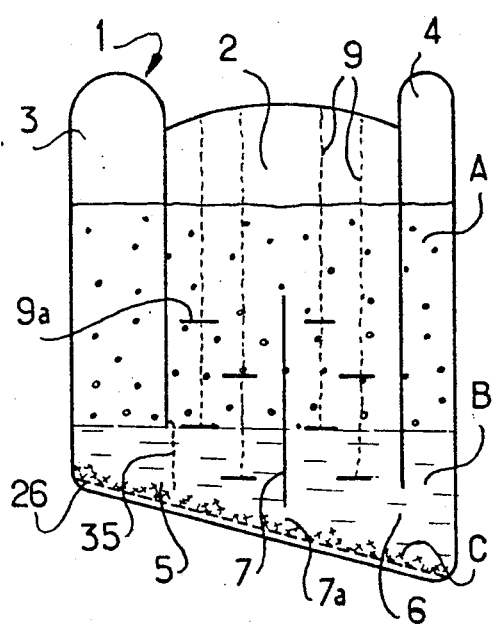
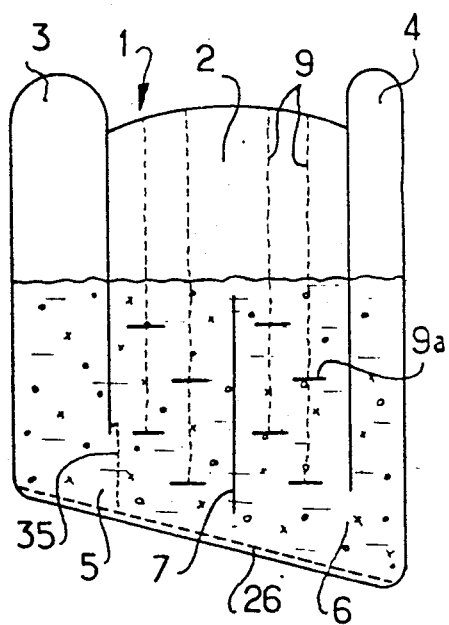
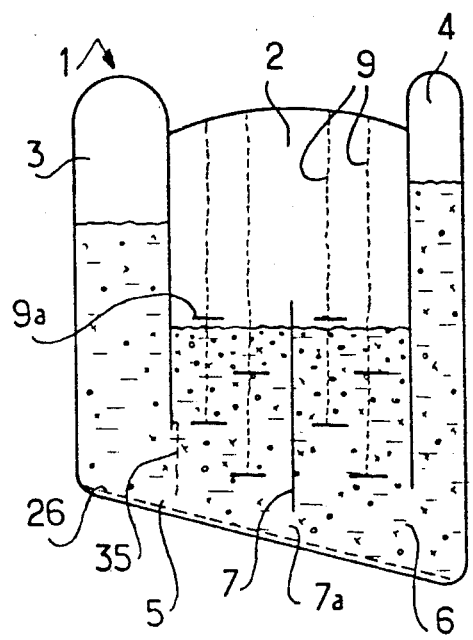
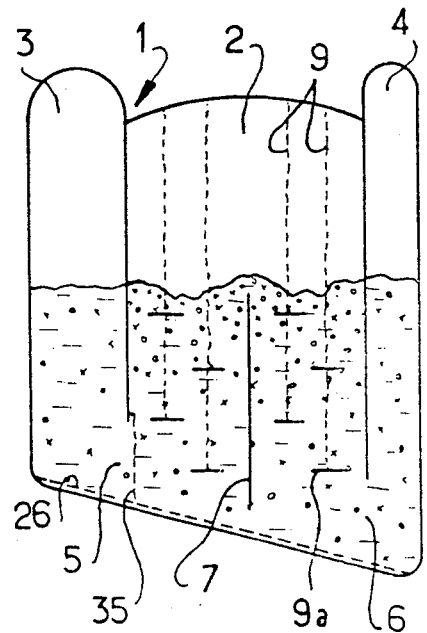

METHOD OF DEGRADING ORGANIC PRODUCTS, BY-PRODUCTS AND SCRAPS IN AN ANAEROBIC MEDIUM

This is a continuation-in-part of application Ser. No. 402,367, filed July 27, 1982, now abandoned.

BACKGROUND OF THE INVENTION

The present invention relates to a method and an apparatus or plant for carrying out the degradation of organic products, by-products and scraps or waste from human, animal and/or vegetable origin.

More specifically the subject matter of the invention is a process and a device for performing a continuous methanizing of solid and/or liquid organic compounds.

Organic materials from various sources such as human, animal or vegetable origin may lead through successive or simultaneous microbiological degradations in an anaerobic medium to gaseous compounds the most important of which are methane and carbon dioxide.

The nature and composition of these organic products are very variable and they consist of more or less polymerized and imbricate elements. These organic products would mostly form a solid substrate whether fibrous or not with a high content of dry matter. This is in particular the case of town and agricultural refuse, garbage or litter for instance. Such products may however also be liquid with small contents of dry matter such for instance as the sludges from purification plants or stations, liquid manures, milk serum.

The major part of such substrates consists of ternary compounds such as sugars, starches, hemicelluloses, celluloses and lignins but quartenary substances such as protides and peptides may also be associated therewith.

The agents participating in such degradations are generally coming from animal, plant and telluric habitats. Numerous species or kinds have been found out. They are evolving within mediums with very variable pH and reduction-oxidation potential with ranges differing with the psychrophilous mesophilous or thermophilous kinds.

In a simplified manner the degradation of an organic matter and in particular of an insoluble organic matter in an anaerobic medium would proceed according to three steps:

a hydrolysis step during which the enzymes would convert the insoluble compounds into soluble substances;

an acidogenous step during which dissolved organic matters are converted into compounds such as fatty acid, alcohol or others. During that acidogenous step there is an acetogenous step during which is generated acetic acid which is one of the compounds which are essential for the formation of methane during the following last step:

a methanogenous step during which methane and carbon dioxide are produced.

Fermentation processes are already known which consist in using digestion tanks, vats or like vessels operating continuously or discontinuously (batch production). The batch-wise or discontinuously operating tanks are used especially with organic products or solid and heterogeneous substrates and are neither convenient nor industrially profitable. The continuously operating digestion tanks are almost essentially used with liquid effluents with a small content of dry matter. In such devices indeed, the treatment of a solid substrate whether heterogeneous or not involves many difficulties in particular in connection with the circulation and homogenization of the substrate within the tank thereby resulting in bad operating conditions and strongly disturbing or interfering with the process of degradation of organic matter. The efficiencies or yields of such plants are relatively low. To provide for a methanizing under suitable conditions, it was therefore necessary to use a liquid substrate or a substrate greatly diluted through addition of water. This amount of water associated with the substrate to be processed would result in the occurrence of polluting liquid refuse and the use of bulky tanks.

From the French patent specification publication No. 2,305,113 is for instance known an apparatus for the digestion of organic matters wherein the material to be processed after having been damped or moistened is fed into a cylindrical compartment wherein it undergoes an aerobic fermentation under pressure and is then driven or pushed by a ramming piston through a bent syphon into a small anaerobic fermentation compartment and thereafter into a large compartment. Within the bend or elbow of the syphon forks would prevent the material from flowing back. According to said patent specification, there is also provided an extraction shaft or well wherein the fermented matter is carried along by a claw.

SUMMARY OF THE INVENTION

The object of the present invention is to remove such difficulties by providing a method of and an apparatus for performing the anaerobic fermentation of organic products, by-products or waste or refuse of human, animal or plant origin in particular with a high content of dry matters whether heterogeneous or not while effecting a good homogenization of the products within the digestion tank to thereby promote on the one hand the process of degradation of the organic material and on the other hand the circulation of the products within the tank through an effect of fluidization of the mass of products.

For that purpose, the invention provides a method of carrying out a degradation in an anaerobic medium for instance a methanogenesis of organic products, by-products or waste from human, animal and/or vegetable origin consisting in feeding said products to be degraded into a closed vessel after having possible sowed or seeded said products with a suitable substrate, forcing said products to follow a direction of circulation within said vessel, recovering or collecting the gas called biogas evolved above said mass of products and discharging the degraded products, said method being characterized by the step of carrying out the feeding and discharge of the products to be degraded pneumatically for instance through a pneumatic thrust. This pneumatic thrust can be caused through injection of gas, preferably biogas.

With such a pneumatic feeding and discharge of the products the processing is unexpectedly improved notably by the fact that the problems of blocking or clogging and corrosion in connection with mechanical devices for supplying or extracting the substrate are removed. Also, the construction of the apparatus is simplified and it is further possible to treat products or substrates having a very high content in dry matters whether heterogeneous or not.

According to one embodiment of the invention method, said method comprises causing the pressure of biogas contained within said closed vessel to suddenly and sharply drop intermittently thereby inducing a flux and reflux or back and forth motion of the mass of products within said vessel.

According to another characterizing feature of the invention method, it is performed an injection of produced biogas into the mass of products contained within said vessel, preferably through emission of short jets or blasts by intermittence under pressure.

According to a preferred embodiment of the invention method, said method further comprises sub-dividing said closed vessel into a plurality of sections; and injecting intermittently biogas, preferably produced biogas, into each one of said sections under a pressure and during a period of time predetermined, set in relation to the density of the products within the involved section. Accordingly, according to the invention method, the pressure of the injection of biogas and the duration of injection is adapted in relation to the actual density of the solid products or of the substrate in the injected section. It can therefore be easily understood that it is obtained with the invention an essentially perfect fluidization of the products during their flow throughout the fermentation vessel.

Further, according to a still preferred embodiment of the invention process, biogas is introduced into each section successively, i.e. displaced or shifted in the time, so as to obtain in practice a rotation of the biogas injection within the vessel, from a section to another one. This rotation of biogas injection can be regular or irregular, i.e. said injection can begin from a given section and be followed by injection in another section not adjacent to the just previously injected section, said first injected section, being selected in view of its actual density and fluidization effect to be reached.

Also, according to the invention method, the biogas injection can be programmed. Such a programmation can be performed with the aid of any means known to one skilled in the art and in particular through use of a microprocessor or a computer.

The invention is also directed to an apparatus or plant for carrying out the method described hereinabove and which is of the kind comprising a reactor or digestor with an anaerobic fermentation vessel, tank or vat provided with substrate feeding means and substrate discharging means, respectively, a gas or biogas outlet connected to a gasometer or like gas holding vessel, wherein the improvement is characterized in that the fermentation vessel comprises a partition wall dividing said vessel into a first part and a second part, said partition wall having a height smaller than that of the vessel, said first part being connected to said substrate feeding means and said second part being connected to said substrate discharging means, at least one of said substrate feeding means and said substrate discharging means comprising means for introducing gas under pressure so as to yield a pneumatic thrust of the products to be degraded into said vessel. This gas is preferably biogas.

According to a particular embodiment of the invention apparatus, each of said substrate feeding means and substrate discharging means comprises a substantially vertical shaft which can be closed and at the top of which is connected said biogas introduction means so as to yield said pneumatic thrust in said shaft.

According to another characterizing feature of the invention apparatus, said biogas outlet is connected to said gasometer through a gate or valve and in particular a hydraulic valve.

According to a still further characterizing feature of the invention apparatus, said fermentation vessel is provided with a plurality of biogas injection ducts, laterally spaced one with respect to the other and located at least in the major portion of said vessel, said biogas injection ducts being fed individually or by groups with biogas through independent gates or valves, thereby subdividing the fermentation vessel into biogas independently fed sections.

According to an advantageous embodiment of the invention apparatus, the biogas injection circuitry comprises a biogas storage container in which biogas is gathered and stored until obtention of a pressure at least equal to the highest pressure required in one of said vessel sections.

According to the invention, each gate or valve is foreseen and designed so as to provide a pressure in relation to the density of the products within the associated or related section.

According to a preferred embodiment of the invention, said apparatus further comprises a programmed control device for each gate or valve of each section.

According to a still further preferred embodiment of the invention apparatus, said apparatus further comprises a biogas injection conduit at the top of the fermentation vessel provided with an appropriate gate or valve, thereby allowing possibility of performing a pneumatic thrust in the fermentation vessel, which is preferably performed simultaneously to the extraction or discharge of the fermented products from the fermentation vessel for instance in direction to the substrate discharging means.

Furthermore, said partition wall splitting the fermentation vessel into a first and a second part is preferably formed with a passageway for communication between said first and second parts at least at the bottom of the vessel.

According to still another characterizing feature of the invention, the apparatus comprises a compressor the inlet of which is at least connected to said gasometer and the outlet of which is connected notably to said plurality of ducts or pipelines opening into the bottom of the vessel, said ducts being advantageously fitted with a check or non-return valve or gate. These ducts or pipelines opening into the bottom of the vessel may possibly be provided with a valve for blowing biogas in successive short jets.

Moreover, said compressor outlet is also preferably connected to ducts or pipelines opening into the bottom of said feeding and discharge shafts and/or to ducts opening at the tops of said feed and discharge shafts, each duct being fitted with at least one shut-off valve. It is thus possible to re-cycle the biogas to all the parts of the apparatus.

In addition, the apparatus can also comprise an air compressor, the outlet of which is connected to said feed shaft and/or discharge shaft for thereby inducing or continuing if desired a degradation in an aerobic medium within the feed shaft and accelerating the process of conversion of the substrate within the discharge shaft with a view to being used as a compost.

The apparatus also comprises means for re-cycling into said reactor and/or into the feed shaft or the discharge shaft the liquid separated from the fermented solid products recovered at the outlet of said discharge shaft, this liquid being a leaven or an inoculum.

According to still another feature of the invention, the feed shaft is provided with two series of slots or slits spaced by some distance from each other and located at some distance from the cover or lid and the bottom end of the shaft, respectively.

Moreover, said valve controlling the discharge of biogas produced within the vessel can be located either outside of the vessel or within the shaft whereas the gasometer is either outside of the vessel or above the latter. In the latter case, the gas would escape through a pipe which extends through the vessel and leads to a condensing syphon adapted to collect or gather the water present within the biogas originating from the fermentation. Preferably, these gases are then carried to a purifier like scrubber, cleaner or filter.

Furthermore, according to a first embodiment of the fermentation vessel or reactor of the invention, said feed and discharge shafts are located near each other, said partition wall being arranged vertically between both end openings of said shafts leading into the vessel and such partition wall having a width smaller than the width of said vessel and a height smaller than the height of the vessel, whereas the bottom of the latter exhibits a double slope and is advantageously of elliptic shape.

According to another embodiment of the fermentation vessel of the apparatus, said feed and discharge shafts are arranged in substantially diametrically opposed relationship on the periphery of said fermentation vessel, said partition wall being arranged vertically and directed substantially along a diameter of the vessel and having a height smaller than that of the vessel. The bottom of this vessel preferably has a single slope or pitch whereas said partition wall is formed with a passageway at its lower portion.

Lastly, the apparatus comprises heat exchangers for carrying out various heat exchanges between the fluids flowing within the apparatus and in particular for heating up the leaven or inoculum before its being fed into the fermentation vessel or reactor or digestor.

BRIEF DESCRIPTION OF THE DRAWINGS

The invention will be fully and completely understood and further characterizing features, details and advantages thereof will appear clearly as the following explanatory description proceeds, with reference to the accompanying diagrammatic drawings given by way of non-limiting examples only, illustrating various embodiments of the invention and wherein:

FIG. 5 is a view in vertical section of another embodiment of the apparatus according to the invention, with parts broken away;

FIG. 6 is a view in cross-section taken upon the line VI—VI of FIG. 5;

FIGS. 7 and 8 are conspectus or block diagrams of the apparatus of the invention with all the biogas circuitry;

FIG. 9 is a conspectus or block diagram of another embodiment of the invention apparatus and biogas circuitry;

FIGS. 10a, 10b, 11a, 11b are schematic views of the fermentation vessel of the invention apparatus to show the results of the method according to the invention on the state of the substrate within the fermentation vessel;

DESCRIPTION OF THE PREFERRED EMBODIMENTS

Figure 12:
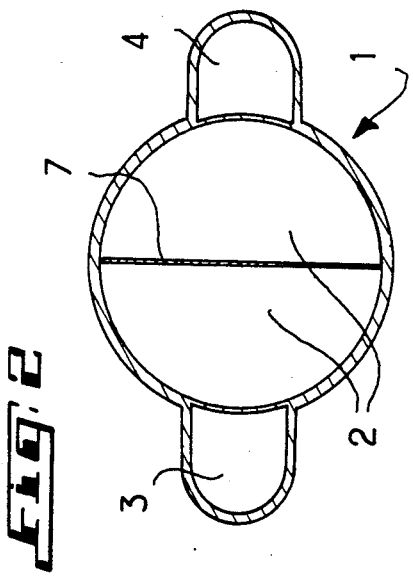
FIG. 12 is a schematic view showing an apparatus for treating the fermented substrate at the output of the fermentation vessel.
Figure 2:
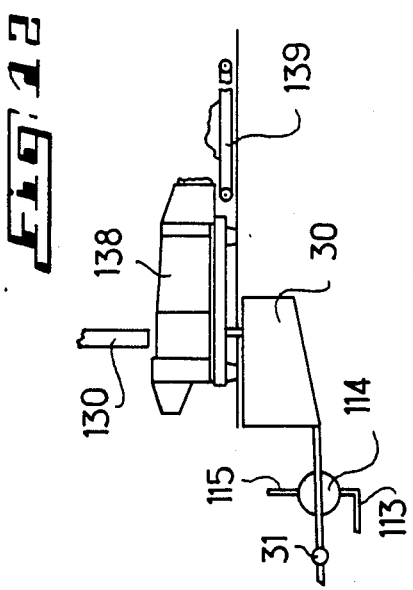
FIG. 2 is a view in cross-section taken upon the line II—II of FIG. 1.
Figure 1:
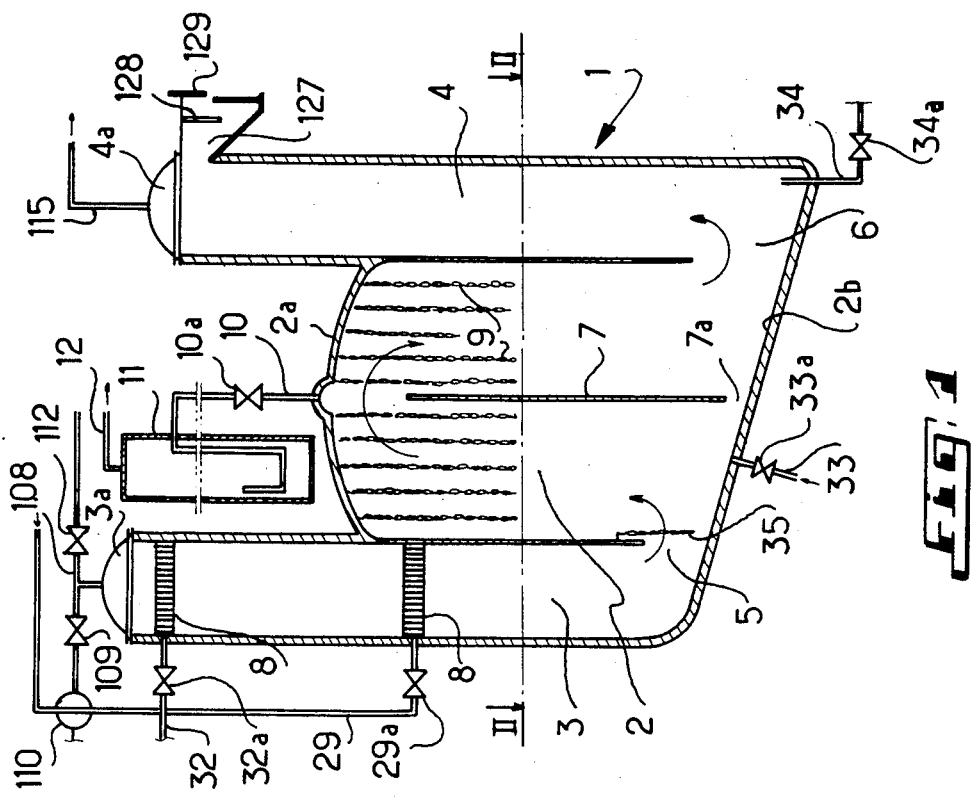
FIG. 1 is a vertical section through an embodiment of the apparatus according to the invention.

Referring to FIGS. 1 and 2, a first embodiment of the invention apparatus or plant and in particular a first embodiment of the fermentation vessel or reactor thereof will be described.

The fermentation portion or reactor 1 of the invention apparatus comprises a substrate feeding or supply means 3 here constituted by a substantially vertical shaft, closable in fully sealing or fluid-tight relationship by a cover or lid 3a, a fermentation vessel 2 with a dome-shaped cover 2a and a substrate discharging means 4, here constituted by a substantially vertical shaft, closable by a cover or lid 4a. The fermentation vessel 2 is separated by a partition wall 7 into a first part and a second part. The first part is connected to feeding means 3 and the second part is connected to discharge means 4. The partition wall 7 is here shown positioned substantially along a diameter of the vessel 2 and having a height smaller than that of the vessel 2. Moreover, this partition wall 7 preferably leaves a passageway 7a at its lower portion, i.e. in the vicinity of the bottom of the vessel 2.

In the embodiment shown on FIG. 1 and as clearly seen on FIG. 2, the feed and discharge shafts 3 and 4 are arranged in diametrically opposite relationship on the periphery of the vessel 2 and are connected to the first and second parts, respectively, of the vessel 2 through syphons 5, 6. The syphon 5 may possibly be fitted with a means such as chains 35 flexible in one direction only and breaking or preventing any backflow or return of the substrate during the anaerobic fermentation towards the feed shaft 3.

The vessel 2 comprises a gas outlet duct or pipeline 10 fitted with a shut-off valve 10a and opening in the shown embodiment into a hydraulic valve 11, the gas or biogas then evolving through the duct or pipeline 12 to flow to a gasometer 15 not shown on FIG. 1.

The feed shaft also comprises two series of slots or slits 8 spaced from each other on the feed shaft 3 and circumferentially located thereon.

The vessel 2 can also comprise chains 9 suspended from the dome-like portion 2a of the vessel 2, the function of which will be described later.

In the embodiment shown on FIG. 1, the discharge shaft 4 is provided at its top with a cover 4a fitted with a gas duct or pipeline 115, an outlet syphon 127 and an outfall or like overflow chute or spillway 128 with an adjustable opening or outlet port 129.

Furthermore, the apparatus 1 comprises several ducts either for draining away the gases from the discharge or feed shaft or for feeding air into this discharge or feed shaft or for feeding leaven or inoculum into the vessel 2. These various ducts will be described more in detail together with the description of the ducts of the apparatus.

Figure 4:
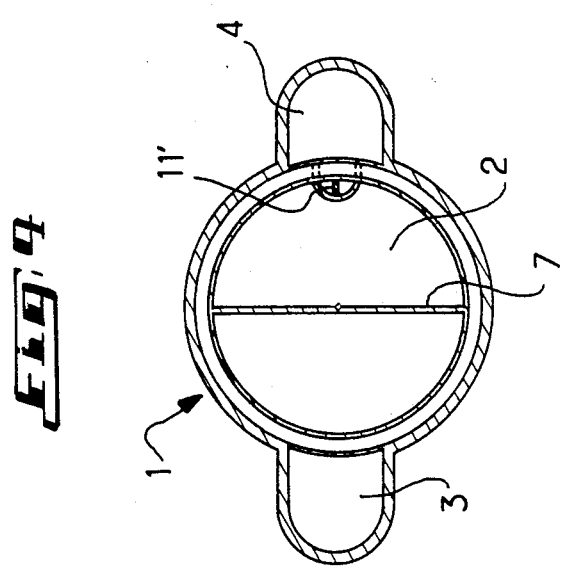
FIG. 4 is a view in cross-section taken upon the line IV—IV of FIG. 3.
Figure 3:
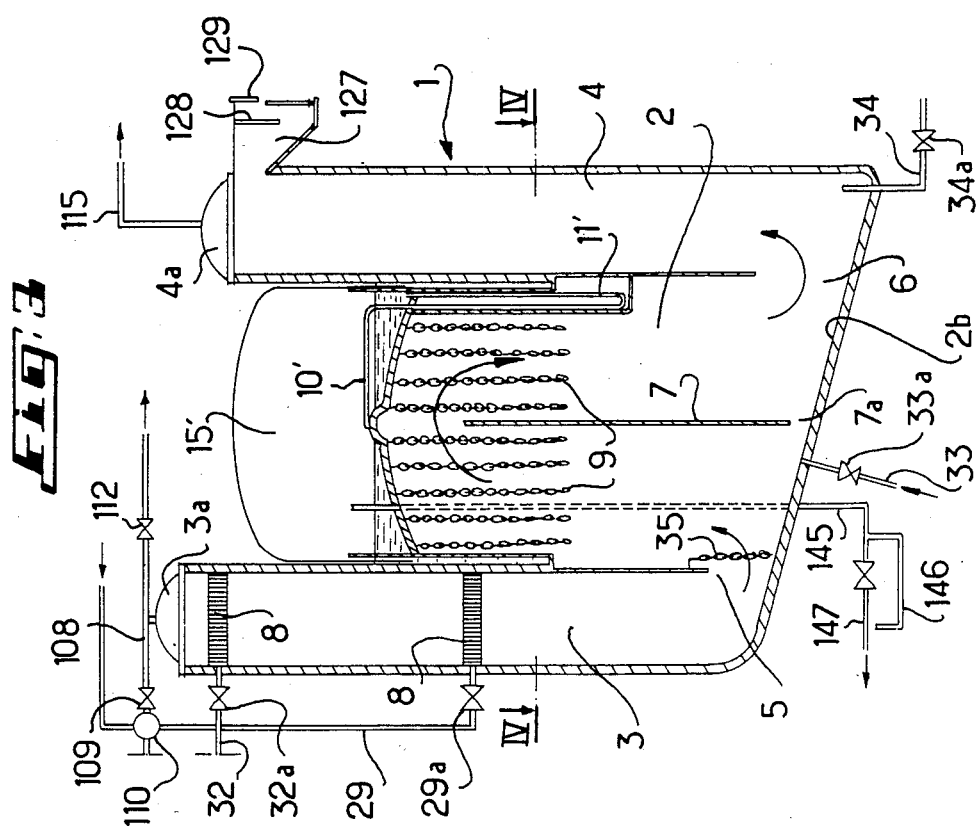
FIG. 3 is a view in vertical section showing another embodiment of the apparatus according to the invention.

The second embodiment of the apparatus 1 according to the invention shown on FIGS. 3 and 4 differs from the first embodiment in that the hydraulic valve 11' is arranged within the reactor vessel 2, the latter being topped by a gasometer 15'. The valve 11' is fitted on a duct 10' one end of which extends as the pipe 10 on FIG. 1 from the top 2a of the vessel whereas its other end opens into the gasometer 15'. Into the latter opens a pipe 145 which leads on the one hand to a condensing syphon 146 adapted to collect or recover the water present within the hot gases or biogases evolving from the fermentation and which is condensing within the pipe 145 and on the other hand to a duct for conveying the biogas produced for instance into a purifier, cleaner, scrubber or like filter means, a shut-off valve 147 being provided on the duct 145.

In both of the embodiments described, the fermentation vessel bottom 2b has one single slope or pitch and the inlet syphon 5 is located at a higher level than that of the syphon 6.

The embodiment of the invention apparatus shown on FIGS. 5 and 6 differs from both previous embodiments in that the shafts 3 and 4 are arranged near each other on the periphery of the vessel 2. The partition wall 7 is then located between the inlets of both syphons 5, 6 within the fermentation vessel 2, its width being smaller than the width of the vessel so that the substrate may flow in the direction of the arrow F. Moreover, as in both embodiments, the height of the partition wall 7 is smaller than that of the vessel 2. In this embodiment, the syphon 5 associated with the feed shaft 3 is also positioned at a higher level than that of the syphon 6 associated with the discharge shaft 4. The bottom 2b of the fermentation vessel 2 exhibits a double slope or pitch and is advantageously of elliptic shape.

Furthermore, the chains 9 fastened to the dome-shaped top 2a of the vessel 2 advantageously carry weighty or heavy elements 9a such as metal discs, these discs being fastened to the chains 9 preferably at the lower portions thereof. Thus the chains 9 are suspended from the dome-shaped top 2a of the vessel so as to hang freely down into the vessel for being embedded at least partially into the substrate to be processed as clearly shown on FIGS. 10a, 10b, 11a, 11b. It is of course possible to arrange these chains 9 together with the weighty or heavy elements 9a within the vessel shown on FIGS. 1 to 4.

Moreover, according to another alternative embodiment of the invention, the outlet syphon 127, the outfall or like overflow-shoot or spillway 128 provided on the discharge shaft 4 may be substituted for by a drain or egress duct fitted with a shut-off valve (not shown).

Referring to FIGS. 7 to 9, the apparatus according to the invention and in particular the various fluid-carrying ducts thereof will now be described.

For the sake of a better understanding of these drawings those ducts wherein the biogas is flowing are shown in heavy solid lines whereas those ducts which carry the leaven or inoculum are shown in thin solid lines and those ducts wherein air is flowing are shown in broken or dotted lines.

In the whole apparatus or plant as shown on FIG. 9, the fermentation vessel 2 is connected to the hydraulic valve 11 through a gas outlet duct 10 fitted advantageously with a shut-off valve 10a. The hydraulic valve 11 is in turn connected to the gas holding vessel or gasometer 15 through a duct or pipeline 12 in which are mounted for instance a gasometer 14 and a container 13 forming a buffer gasometer.

It must be noted that a gate or valve actuated for instance pneumatically, electrically, hydraulically, electromechanically and so on can be substituted for the hydraulic valve 11 for the same purpose.

The gasometer 15 is fitted with an outlet duct 16 provided with a shut-off valve 16a and which is connected on the one hand to a duct 17 for carrying the gas for instance to a purifier, a storage station or a burner, and, on the other hand, to the inlet of a gas compressor or booster 18 to provide for the circulation of the biogas within the whole apparatus or plant. The outlet 19 of this gas compressor or booster 18 is connected through a duct 21 and branch ducts 22 and 23 through valves 22a, 23a to the top portions of the feed and discharge shafts 3,4, respectively with the purpose of providing the pneumatic thrust of the substrate as previously emphasized.

The outlet 19 of the booster 18 is also connected through a duct 20 fitted with a valve 20a to the bottom portions of the feed and discharge shafts 3,4 through the ducts 24,25; and to the bottom portion of the vessel 2 through a plurality of ducts 26, with, in the latter case, the purpose of injecting biogas at the bottom of the fermentation vessel 2. A preferred embodiment of said ducts will be described with reference to FIG. 13.

On the other hand, the top portion of the fermentation vessel 2 is connected to the inlet of the compressor 18 through a duct 27 fitted with a valve 27a.

According to a preferred alternative of this embodiment, the top portion of the fermentation vessel 2 can be connected to the outlet of the compressor 18 through a derivation duct 23' to duct 23 fitted with an associated valve 23'a with the purpose of performing a pneumatic thrust within the fermentation vessel 2 through injection of biogas through valve 23'a at the top of the fermentation vessel 2 simultaneously to the cutting off of the pneumatic thrust within discharge shaft 4.

Preferably, the ducts 26 opening into the bottom of the fermentation vessel 2 and the ducts 24,25 are fitted with check or non-return valves (not shown) for preventing materials contained within the vessel from falling into said ducts. Moreover, the ducts 26 may possibly be provided with valve means (not shown) adapted to emit short and successive jets under pressure.

The gas circuit shown on FIG. 9 described hereinbelow is given by way of illustrative example only. It is of course possible to provide other ducts or devices, valves, gates or the like for carrying out any possible circuits for the flow of gas within the vessel and for instance to provide heat exchanges with other fluids within the apparatus or plant as shown on FIGS. 7 and 8.

In these Figures, the circuit for re-cycling the biogas within the apparatus is not shown.

One fraction of the biogas recovered within the gasometer 15 is directly fed into the purifier 111 whereas another fraction is put in heat exchanging relationship with the air possibly supplied into the feed shaft 3, within the heat exchanger 110 and then through the ducts 108,113 and valves 109,112, it also undergoes a heat exchange within the heat exchanger 114 with the leaven re-cycled into the apparatus 1. This biogas fraction is then fed into the purifier 111 through the pipeline 115. Advantageously, the biogas present at the upper portions of the feed and discharge shafts is fed into the purifier 111.

The flow circuits of the leaven or inoculum and of the air will be described at the same time as the operation of the plant.

Finally, with reference to FIG. 13, the best mode of the invention apparatus comprises fermentation vessel 2 of the type shown in FIGS. 5 and 6 but modified as follows with respect to introduction of biogas into the fermentation vessel 2 and fed from the gasometer of the type for instance of a gasometer 15 of FIG. 9.

Figure 13:
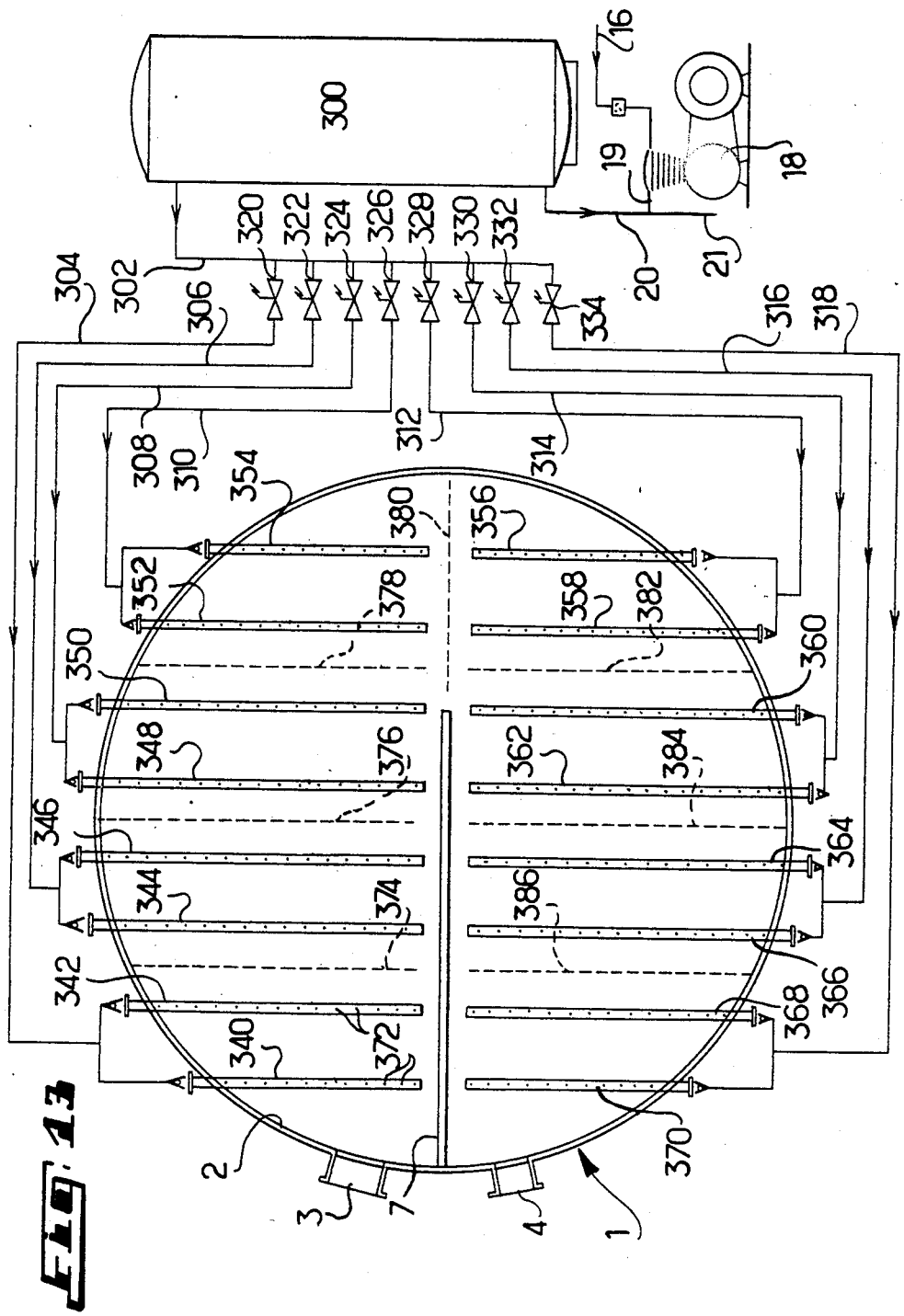
FIG. 13 shows a modification of the invention apparatus subject matter of FIGS. 5 and 6 and is a view in cross-section of the bottom of the fermentation vessel, seen from the top thereof and shows all the biogas circuitry for introduction of biogas in the bottom of the fermentation vessel.

Duct 16 receiving biogas at the outlet of gasometer 15 is shown at the right of FIG. 13. The compressor 18 is provided on this duct 16 as shown in FIG. 9 and the duct 19 connected with the outlet of the compressor 18 is subdivided into ducts 20 and 21 exactly as in the case of FIG. 9.

However, according to the present modified embodiment, duct 20 does not deliver the biogas immediately to the bottom of the fermentation vessel 2 but is connected to a biogas storage container 300 able to support a high pressure and in which biogas is gathered and stored until obtention of a predetermined high pressure which will be defined later.

A duct 302 is connected to the outlet of said biogas storage reservoir 300, said duct 302 being sub-divided into a plurality of sub-ducts 304,306,308,310,312,314,316,318, each being provided with an individual gate or valve, respectively 320-322-324-326-328-330-332-334.

The sub-ducts 304 to 318 are feeding biogas to a plurality of biogas injection ducts 340,342,344,346,348,350,352,354,356,358,360,362,364,366,368,370 which are located in the locaion of the bottom of fermentation vessel 2 and which are constituted by hollow tubes of appropriate section longitudinally provided with a plurality of injection openings such as 372.

According to the present invention, said plurality of biogas injection ducts 340 to 370 is fed with biogas individually or in groups, for instance two by two as shown on FIG. 13, via the independent valves 320 to 334 so as to sub-divide the fermentation vessel 2 in sections independently fed with biogas. The limits of the sections have been symbolically materialized on FIG. 13 by the presence of the dotted lines 374,376,378,380,382,384,386. In the embodiment shown on FIG. 13, it thus appears that eight sections have been defined. It will be noted that the biogas injection ducts are laterally spaced between them and located at least in the major portion of the fermentation vessel 2, preferably regularly as shown. Further, the specific construction of the biogas injection ducts 340 to 370 is a part of the invention.

Further, according to the present invention, each valve 320 to 334 is foreseen designed or constructed so as to provide a pressure in relation to the density of the products in the associated section. Besides, each valve is controlled preferably according to the invention through a programmed control device (not shown), so as to inject intermittently biogas into each of the sections of the fermentation vessel 2 under pressure and during a period of time predetermined, set in relation to the density of the products in the associated section.

By the terms "pressure of injection in relation to the density of the products in a given section"—it is intended to emphasize that the injection pressure is sufficient to yield a fluidization of the mass of the products or substrate to be fermented or in fermentation having the said density.

It will thus be understood that the injection pressure is actually commensurate or adapted to the actual density of the mass of products or substrate in the section where is injected biogas.

Thus, with the invention apparatus, the previously set forth method is performed, namely the obtention of a sub-dividing of the fermentation vessel 2, into a plurality of sections. Further, with a view of performing a substantially perfect or homogeneous fluidization of the solid products or substrate within the fermentation vessel 2, the invention method comprises injecting intermittently biogas into each one of the sections under pressure and during a period of time predetermined, set in function of the density of the products within the associated section.

Further, according to a further characterizing feature of the invention method, biogas is injected into each section successively while being shifted in the time so as to obtain a so-called biogas injection rotation within the fermentation vessel 2 from a section to the other. This injection can be regular or irregular and therefore a given section can be injected with biogas whereas one or several of the adjacent sections are not injected with biogas should in said sections the fluidization of the products be satisfactory, i.e. the density of the products. Besides, with the aid of the programmed control device, it can be obtained a programmed injection. This programmation can be automatically servo-controlled by means detecting a lack of fluidity within one of the sections of the fermentation vessel 2 so as to immediately order an injection in the concerned section by acting on the corresponding valve.

It should also be noted that according to the present invention, the presence of the biogas storage revervoir 300 provides unexpectedly for one skilled in the art the use of a compressor 18 of low capacity, namely with a low compression ratio.

Further, with the presence of duct 23', FIG. 9, for injection of biogas at the top of the fermentation vessel 2, it can be performed a pneumatic thrust from the top of the fermentation vessel 2 so as to easier discharge the solid products flowing on the bottom of the fermentation vessel 2 towards the discharge shaft 4. Preferably, according to a further characterizing feature of the invention method, the pneumatic thrust in the fermentation vessel 2 is performed simultaneously with the pneumatic thrust in the discharge shaft 4. Further, according to the invention method, the previously said pneumatic thrust in the substrate feeding shaft 4 is performed simultaneously to the setting to opening of biogas evacuating valve such as valve 10a of FIGS. 1 to 9, thereby improving the forced feeding of the products or substrate to be fermented.

It is therefore clear for one skilled in the art that according to the invention, it is obtained a practically perfect fluidization of the products or substrate even with a high content in solid materials such as human waste products and litter together with a simplified technology of the manufacturer of the fermentation vessel, in particular with the sub-dividing of the fermentation vessel into a plurality of independent sections as in the case of the embodiment of FIG. 13 by lowering the slope of the bottom of the fermentation vessel, thereby yielding a lowering of the vessel costs.

Further, it is of course also obtained according to the invention, unexpectedly, an improved yield in biogas.

The working of the invention apparatus will now be described.

Organic products, by-products or waste from human, animal or vegetable origin are possibly subjected to a mechanical, physical, chemical or microbiological preliminary treatment, for instance to a heat processing, a pounding, crushing or milling or a chopping through a chopper-projector, a quick depressurization or pressure drop, an anaerobic pre-fermentation to for instance promote the hydrolysis of the matter, the defiberization, shredding or delignification in particular in the case of cellulosic and ligno-cellulosic compounds. After the opening of the cover 3a the materials are then supplied into the feed shaft 3. The cover is then closed again in sealing or fluid-tight relationship. Thereafter a gas is supplied into the top portion of the feed shaft 3 to build up a gas pressure, for instance through injection of compressed air produced by the compressor 28 and conveyed through the pipeline 29 to the lower portion of the feed shaft 3 or by feeding biogas through the pipeline 23 upon opening the shut-off valve 23a. The gas pressure prevailing at the bottom portion of the feed shaft 3 would drive or push the products or substrates through the syphon 5 for feeding same into the first portion of the fermentation vessel 2.

The injection of air into the feed shaft 3 is carried out if it is desirable to oxygenate the substrate supplied or to induce, proceed with or continue a thermogenous aerobic fermentation of the substrate in accordance with the nature of the substrate to be treated.

The substrate is thus fed into the first portion of the fermentation vessel 2 and through an upward motion would be poured into the second portion of the fermentation vessel 2 through overflow over the partition wall 7 and then after a downward motion would pass through the syphon 6 to rise within the discharge shaft 4 where one part will be periodically discharged by the syphon or spout 127 through opening of the cover 4a. It is also advantageous to inject the air into the discharge shaft 4 through the pipeline 36 for accelerating the process of conversion of the fermented substrate with a view of using same as a compost.

As known per se and advantageously the substrate recovered at the outlet of the discharge shaft 4 is fed through a spill-way or overflow shott 130 into a press 138 which would separate the fermented solid part from the liquid or leaven and which may possibly be subjected to an injection of air. A conveyor belt 139 removes the solid matter whereas the liquid is recovered or collected in a vat 30. This leaven or inoculum thus recovered may be used in various manners and may be re-cycled under the action of a pump 31 to the various portions of the reactor 1 after having possibly been reheated in the heat exchanger 114. It may thus be:

re-cycled into the upper portion of the feed shaft 3 through the duct 32, in particular if a preliminary thermogenous aerobic treatment is carried out in the feed shaft 3, or injected into the bottom portion of the fermentation vessel 2 through the ducts 33 or conveyed into the bottom portion of the discharge shaft 4 through the duct 34.

These various ducts are advantageously provided with valves 32a, 33a and 34a, respectively.

The nature of the substrate processed within such a plant may be very variable.

Moreover, the plant and the process according to the invention make it possible to conduct an anaerobic fermentation of organic products and in particular a methanogenesis with a substrate having a small content of dry matters or with a substrate having a high content of dry matter, of about 30% for instance or more and whether very heterogeneous or not.

Referring to FIG. 10a indeed without any stirring and homogenization of the substrate in the reactor, a first layer A loaded with gas and a lower liquid layer B will be obtained very quickly, heavy materials C having been separated or allowed to settle onto the bottom of the reactor. Within the layer A will then be built up a crust or cover which would obstruct or clog the reactor thereby preventing any circulation of the substrate and thus blocking or discontinuing the continuous operation of the digestor and causing the fermentation to stop.

According to the invention, to promote the anaerobic degradation process within the reactor a homogenization and a fluidization of the substrate are carried out by using the biogas produced. Such a homogenization and fluidization are in the embodiment of the invention carried out through the combination of several effects connected with the re-cycling of the biogas within the substrate, with the flux and reflux motion of the substrate between the fermentation tank and the feed shaft 3 and/or discharge shaft 4 and at last with the movements of the chains 9 and discs 9a which latter can be absent.

On FIG. 10b has been diagrammatically illustrated the state of the substrate when a recirculation or bubbling of the biogas within said substrate is merely performed. This injection of biogas into the substrate is carried out by means of a compressor 18 either through the ducts 22, 23 or through the ducts 24, 25 or through the ducts 26 or through one or several of these ducts by the opening or closing of the valves 20a, 22a, 23a, 24a, 25a.

Such a recirculation of biogas however if it is carried out alone is especially effective for the treatment of a substrate with a small content of dry matters providing for a scattering of the heavy products C and a better distribution of the het supplied to the reactor 1.

On FIGS. 11a, 11b has been shown the condition of the substrate in the case where the three combined effects of gas recirculation, the flux and reflux motions of the substrate and the movements of the chains 9 are applied.

The flux and reflux or back and forth motion of the body of substrate between the vessel 2 and the feed and discharge shafts 3, 4 is achieved by means of the hydraulic valve 11 through which the pressure of the biogas contained above the substrate within the fermentation vessel 2 may be raised. During that time period the substrate is driven or forced into the discharge shaft 4 and/or the feed shaft 3 (FIG. 11a). When the pressure threshold is reached the hydraulic valve 11 enables the biogas to evolve towards the buffer gasometer 13 and the pressure prevailing within the fermentation vessel 2 suddenly drops and causes the substrate to flow back into said fermentation tank to reach its initial level again (FIG. 11b). Moreover, the back and forth or flux and reflux motions of the substrate would induce the movements of the chains 9 kept stiff by the weighty or heavy elements 9a, thereby breaking the top surface or cover crust of the substrate which would build up during the methanization. The moistening or damping of this broken cover crust is effected forthwith thereby avoiding the formation of a crust through dehydration which may clog, choke or obstruct the reactor with time.

Moreover the chains 9 and discs 9a form preferential paths of travel for the evolution of the biogas within the substrate.

Thus, under the combined effect of the recirculation of biogas, of the hydraulic valve and of the chains and discs a substantial stirring of the substrate is achieved thereby enabling same to be fluidized when the latter has a high content of dry matters. Furthermore due to the biogas recirculation, the accumulation or gathering of heavy materials settled down onto the bottom of the reactor may be avoided. It is thus possible to extract through the discharge shaft 4 a substrate in the form of a thick paste heavily loaded with dry matters.

The method and the plant according to the invention will thus make it possible to treat under conditions very favourable for achieving a good anaerobic degradation a substrate with a small content of dry matters as well as a substrate with a high content of dry matters. It is thus possible on the one hand to substantially decrease the bulk or capacity of the fermentation tanks and on the other hand to provide for better conditions of development of the various steps of the process of anaerobic digestion. A substrate heavily loaded with dry matters indeed is a very good physical support for the microbiological populations required for the anaerobic digestion and its buffer capacity is improved during the fermentation. Moreover, due to the high concentration of organic materials within the reactor the gas production is improved and owing to a better fixation of the biomass, the methods of digestion are made reliable and effective.

It should be understood that according to the nature of the substrate, it is possible to merely use the effect of the hydraulic valve combined with the chains 9 or merely the biogas recirculation.

Moreover, the pneumatic drive or forcing of the products within the fermentation vessel 2 through a syphon and their discharge also through a syphon make it possible to periodically feed the substrate to be treated into the feed shaft 3 and to periodically remove or extract the fermented substrate from the discharge shaft 4 while always keeping a body of substrate within the fermentation vessel 2 so as to avoid blocking the continuous operation of the digestor thereby causing the fermentation to stop.

Furthermore, the reactor 1 is advantageously fitted with a heating system which will keep the tank at the desired temperature to promote the anaerobic degradation process and such a heating system may for instance be integrated into the double bottom of the tank shown on FIG. 5. Moreover the reactor 1 and the various pipelines are fully insulated thermally for limiting the energy losses. For that purpose various heat exchangers are provided between the fluids within the plants as shown on FIGS. 7 and 8 or for instance the leaven or inoculum is re-heated through passing same into a digestor located upstream of the reactor 1 wherein is carried out a preliminary treatment of the substrate through thermogenous aerobic degradation in order to thus optimize the power efficiency of the plant.

Moreover, the apparatus comprises, in a known manner, devices for measuring necessary physico-chemical values such as gas flow, temperature, pH, rH and the oxygen concentration.

What is claimed is:

1. Method for carrying out degradation of organic products in an anaerobic medium to form degraded material including biogas, comprising the steps of
   feeding said organic products into a closed vessel, through a first syphon,
   forcing at least a portion of said organic products to follow a pre-determined circuitous direction of circulation around at least one partition in said closed vessel, by application of pneumatic thrust thereto, whereby said organic products are degraded and biogas is evolved within said closed vessel,
   withdrawing the evolved biogas from above said products, and
   discharging the remaining degraded material from said closed vessel through a second syphon situated at a level lower than said first syphon.

2. The method of claim 1, wherein said organic products are downwardly fed into said closed vessel through said first syphon, and forced to circulate upwardly over said partition which extends substantially upwardly in said closed vessel, by application of said pneumatic thrust, and then downwardly through said second syphon, and
   said degraded material is discharged through said second syphon in an upward direction.

3. The method of claim 2, wherein said pneumatic thrust is applied by causing overall gas pressure within said vessel, to vary.

4. The method of claim 3, wherein said overall gas pressure is varied by carrying out at least one of the steps of
   injecting gas into an input shaft communicating with said first syphon and through which said organic products are introduced into said vessel,
   injecting gas into said vessel itself,
   injecting gas into an output shaft communicating with second syphon and through which said degraded material is removed from said vessel, and
   varying the rate at which the evolved biogas is removed from said vessel.

5. The method of claim 4, comprising the additional step of
   recycling at least a portion of said evolved and withdrawn biogas, by carrying out at least one of said injection steps, whereby the biogas constitutes said injected gas.

6. The method of claim 5, comprising the additional step of
   recycling a portion of said discharged and degraded material by carrying out at least one of the following steps of
   injecting a portion of said discharged and degraded material into an upper portion of said input shaft,
   injecting a portion of said degraded material into the bottom of said vessel, and
   injecting a portion of said degrading material into the bottom of said output shaft,
   whereby said flowing organic products are homogenized and fluidized.

7. The method of claim 4, comprising the additional step of
   freely suspending a plurality of weights in said vessel, whereby said weights are caused to oscillate under effect of the circulation of the organic products through said vessel and break up any solidified top layer or crust which might form on top of the circulating organic products.

8. The method of claim 2, comprising the additional step of freely suspending a plurality of weights in said vessel, whereby said weights are caused to oscillate under effect of the circulation of the organic products through said vessel and break up any solidified top layer or crust which might form on top of the circulation organic products.

9. The method of claim 3, wherein the pressure varying induces back and forth motion of the organic products within the vessel.

10. The method of claim 4, wherein the injection of gas into said input shaft is performed substantially simultaneously to the withdrawing of biogas from within said vessel.

11. The method of claim 5, comprising the additional step of
   subdividing said vessel into a plurality of sections, and
   wherein said biogas is recycled by intermittantly injecting the same into each said section at predetermined pressure and for a predetermined period of time and independent from injection into all other sections,
   wherein the pressure and time are determined with respect to density of organic products in each of said sections, and
   whereby fluidity of the circulating organic products within said vessel is ensured.

12. The method of claim 11, wherein the biogas is successively introduced into said vessel from section to section.

13. The method of claim 11, comprising the additional step of
   storing the withdrawn biogas in a reservoir adapted to communicate with said injection sections of said vessel, and at a pressure therein at least equal to an injection pressure into a section having the highest density of organic products.

14. The method of claim 11, comprising the additional step of
   programming the various injections to take place by automatic servo-control based upon the detection of degree of fluidity of organic products in the respective sections.

15. The method of claim 5, wherein said recycled biogas is injected into the vessel itself, and comprising the additional step of
   stopping injection of gas into said output shaft when the biogas is injected into said vessel itself.

16. A method for carrying out degradation of organic products in an anaerobic medium to form degraded organic material including biogas, comprising the steps of
   feeding said organic products into a closed vessel,
   forcing said organic products to follow a predetermined direction of circulation through said vessel, whereby said organic products are degraded and biogas is evolved within said closed vessel,
   withdrawing the evolved biogas,
   discharging the remaining degraded material from said closed vessel,
   subdividing said vessel into a plurality of sections,
   recycling a portion of said withdrawn biogas into said closed vessel in a manner such as to effect the forcing by pneumatic pressure of said organic products to cause the same to follow said predetermined direction of circulation through the vessel, and
   wherein the biogas is recycled by intermittently injecting the same into said section at a predetermined pressure and for a predetermined period of time and independently of the injections into all other sections,
   whereby fluidity of the circulating organic products within said vessel is ensured.

17. The method of claim 16, wherein the pressure and time are determined with respect to density of organic products in each of said sections.

18. The method of claim 17, wherein the biogas is successively introduced into said vessel from section to section.

19. The method of claim 17, comprising the additional step of
   storing the withdrawn biogas in a reservoir adapted to communicate with said injection sections of said vessel, and at a pressure therein at least equal to an injection pressure into a section having the highest density of organic products.

20. The method of claim 17, comprising the additional step of
   programming the various injections to take place by automatic servo-control based upon the detection of degree of fluidity of organic products in the respective sections.

* * * * *